United States Patent [19]

Gazzani

[11] Patent Number: 4,897,214

[45] Date of Patent: * Jan. 30, 1990

[54] SKIN CLEANING PREPARATIONS CONTAINING A HLB 10-19 NON-IONIC EMULSIFIER AND A THICKENING AGENT

[75] Inventor: Giovanni Gazzani, Appiano Gentile, Italy

[73] Assignee: Crinos Industria Farmacobiologica Spa., Como, Italy

[ * ] Notice: The portion of the term of this patent subsequent to Sep. 27, 2005 has been disclaimed.

[21] Appl. No.: 163,396

[22] Filed: Feb. 25, 1988

Related U.S. Application Data

[63] Continuation of Ser. No. 740,293, May 31, 1985, Pat. No. 4,774,016, which is a continuation of Ser. No. 572,942, Jan. 23, 1984, abandoned.

[30] Foreign Application Priority Data

Jan. 24, 1983 [IT] Italy .............................. 19248 A/83

[51] Int. Cl.$^4$ ...................... A61K 7/075; A61K 7/50; C11D 1/66; C11D 3/37
[52] U.S. Cl. .................................. 252/170; 252/173; 252/174.21; 252/DIG. 5; 252/DIG. 13; 424/70
[58] Field of Search ...................... 252/174.17, 174.21, 252/174.22, 174.18, DIG. 1, DIG. 5, DIG. 14

[56] References Cited

U.S. PATENT DOCUMENTS

| | | | |
|---|---|---|---|
| 3,208,949 | 9/1965 | Rosnati | 252/109 |
| 3,749,682 | 7/1973 | Tanner | 252/524 |
| 3,808,329 | 4/1974 | Bolich | 424/70 |
| 4,154,706 | 5/1979 | Kenkare | 252/547 |
| 4,284,533 | 8/1981 | Imamura | 252/542 |
| 4,323,467 | 4/1982 | Fu | 252/106 |
| 4,323,468 | 4/1982 | Grollier | 252/174.17 |
| 4,374,745 | 2/1983 | Sibley | 252/106 |
| 4,508,634 | 4/1985 | Elepano | 252/163 |

FOREIGN PATENT DOCUMENTS 1540386 2/1979 United Kingdom ........... 252/174.22

*Primary Examiner*—Dennis Albrecht
*Attorney, Agent, or Firm*—McAulay Fisher Nissen & Goldberg

[57] ABSTRACT

A preparation for the hygiene and the cleaning of skin, scalp and hair, essentially comprising 5.0% to 10.0% of an emulsifying agent containing an HLB 10-19 nonionic emulsifier and 0.5 to 5.0% of a thickening agent consisting of organic substances forming with the water gels or colloidal solutions. Such a preparation is endowed with a mild and delicate cleaning action, and is surprisingly lacing of any irritating effect.

7 Claims, No Drawings

SKIN CLEANING PREPARATIONS CONTAINING A HLB 10-19 NON-IONIC EMULSIFIER AND A THICKENING AGENT

This application is a Continuation of Application Ser. No. 740,293, filed May 31, 1985, now U.S. Pat. No. 4,774,016, which in turn was a Continuation of Ser. No. 572,942, filed Jan. 23, 1984, now abandoned.

The present invention relates to a preparation for the hygiene and the cleaning of the skin, the scalp and the hair.

It is known that the basic components of the presently commercially available preparations for the hygiene and the cleaning of the skin and, more particularly, of the scalp and of the hair, are the detergent compounds of ionic type.

It is also known that the action of these compounds with respect to the skin, the scalp and the hair is a rather strong fat removing action, which is responsible of a number of drawbacks which to date have not been satisfactorily solved.

In fact, an extreme fat removing effect causes an objectionable stimulation of the sebum secretion, the more frequent is the use of the said preparation the higher is secretion, with the attendant requirement of even more frequent washings.

It is thus possible that a vicious circle is set up which at the very end may induce and/or make worse seborrhea status, with the attendant weakening and possibility of hair fall, undesired irritated layers of the scalp and of the skin being thus formed. These serious and acknowledged drawbacks are furthermore accompanied by aesthetically undesired features, which are only partially relieved by the presence of other ingredients in the formulation of the subject preparations.

The problem essentially faced by the present invention is that of providing a preparation for the hygiene and the cleaning of the skin, the scalp and the hair, the efficacy of which is not based on the cleaning-fat removing action of a detergent compound, particularly of a detergent compound of ionic type, whereby the normal processes of sebum secretion are not altered.

Such a problem is solved according to the invention by means of a preparation for the hygiene and the cleaning of the skin, scalp and hair, comprising as a weight percent of the total weight of the preparation, 5 to 10% of an emulsifying agent and 0.5 to 5% of a thickening agent, the latter consisting or orgaic substances capable of forming with water gels or colloidal solutions.

The problem of the hygiene and cleaning of skin, scalp and hair has been and is very important and the prior art is crowded with suggestions for dealing therewith.

The emulsifying agents, particularly of the non ionic type, were used in the prior art in detergent compositions as well as in cosmetic preparation.

The thickening agents capable of forming, in the presence of water, gels and colloidal solutions, were also well known and used in the prior art.

For instance U.K. Patent 957,157 relates to cosmetic compositions in gel form, wherein a high molecular weight carboxyvinyl resin is added to a solution and then gelified; before the addition of the solution a surface active agent (for instance a non ionic agent, such a polyoxyethylene sorbitan monolaurate or palmitate) is added to promote the wetting of the resin and thus the swelling thereof.

The carboxyvinyl resin is thus used in order to bring the prparation to the state of a gel.

The U.S. Pat. No. 2,771,395 provides hair grooming preparations wherein organic esters, such as those formed by polyoxyalkylene and/or alkylene glycols with fatty acids, are used to promote the solubilization of sodium carboxymethylcellulose.

Besides these ingredients, the subject preparations moreover comprise lower aliphatic alcohols, rubefacients, germicidal agents and perfume oils.

The French published application No. 2,358,877 relates to hair shampooing non ionic compositions with non ionic components, comprising the following ingredients:

(1) water soluble foaming or foam stabilizing agents, preferably trialkylamine oxides.
(2) Non-ionic surface active agents, preferably monoesters of fatty acids with polyoxyethylene hexitan derivatives (e.g. polyoxyethylene sorbitane).
(3) Non-ionic detergents, such as alkoxypolyethylene ethanols and/or alkylglycosides or their mixtures.

Instead of the component (3) foam stabilizers and viscosity controlling agents can be used such as alkanolamides of fatty acids and thickening agents, such as polyamylamides.

Further non-ionic substances can be added to the basic formulation, such as thickening agents (hydroxypropylmethylcellulose), dyeing agents, perfumes, lubrificants etc., provided that the desired cleaning effects is attributed to the above three main ingredients.

The French Patent Application No. 2,323,375 relates to a base composition for the formulation of perfumes, creams lotions, hand cleaning preparations, which compositions comprises as the essential ingredient the product resulting from the thermal condensation of a carboxypolyvinyl polymer, which is heated for 2 minutes to a temperature of between 204° and 315° C.

The said essential ingredient, upon admiwing with water, gives place to a gel which can be added with other ingredients as dyeing agents, surface active agents (e.g. oxyethylates of fatty amines, such as triethanolammonium stearate), emulsifying agents (e.g. polyoxyethylene derivatives of partial esters of a fatty acid and the sorbitan anhydride), and the like.

The European Patent Application No. 0067025 relates to liquid cleansing products comprising:

(a) a thickening agent, such as guar gum or the corresponding hydroxypropyl derivative, in an amount of 0.1 to 1%;
(b) a further thickening agent, selected among the carboxyvinyl polymers or their derivatives, such as polyacrylic acid cross-linked with 1% of polyallyl sucrose, in an amount of 0.15 to 1%;
(c) a surface active agent in an amount of 5 to 30%, of the water soluble type and selected among cationic, anionic, non ionic, amphoteric and zwitterionic compounds.

As it shall appear from the following detailed description of the present invention, the purpose thereof is that of providing an efficacious cleaning action, without the undesirable drawbacks as previously mentioned.

Such a purpose is achieved by means of a mixture of only two types, of compounds which per se are not endowed in a significant manner with such a property and without the presence of glycerides or oils which are normally used to promote the emulsifying and/or cleaning action of compositions for the cleaning of skin (such as for instance in the cleaning milks).

According to the present invention the emulsifying agent useful in the preparation of the invention is a non ionic emulsifying agent having a HLB emulsifying power (Hydrophil-Liophil Balance) preferably of between 10 and 19, and selected in the group comprising:

polyoxyethylenethers of higher alcohols having 10 to 40 and, preferably, 15 to 25 oxyethylene groups. Examples of suitable higher alcohols preferably containing 12 to 18 carbon atoms comprise lauryl, myristyl cetyl, stearyl, oleyl alcohols and cholesterol;

polyoxyethylenesters of fatty acids, having 20 to 100, preferably 20 to 40, oxyethylene groups. Examples of useful and preferred fatty acids, preferably containing 12 to 18 carbon atoms are lauric, myristic, cetylic, stearic, oleic, ricinoileic acids;

polyoxyethylensorbitan esters of fatty acids, heaving 10 to 30, preferably 15 to 20 oxyethylene groups. The preferred fatty acids of above identified are those above referred to;

glycerides and mixtures of glycerides of fatty acids, partially etherified with polyoxyethylene groups;

saccharose esters with the fatty acids of the above listed types;

polyols, for instance sorbitol, mannitol and the like, condensed and propylene with ethylene oxide;

their mixtures.

Examples of thickening agents, useful in the preparation of the present invention, both of vegetal origin and synthetically prepared, comprise alginic acid, and salts and esters thereof, carrageen, pectin, arabic gum, guar gum, tragacauth gum, cellulose derivatives, such as for instance and preferably carboxymethylcellulose, methylcellulose, ethylcellulose, dioxypropylcellulose, and carboxyvinyl polymers commercially known as Carbopol and their mixtures.

In the related art it is well known that the emulsifying agents of the afore said types have no efficacy or show only a limited effect as regards the removal of fat, sebum, and of other impurities from the skin, the scalp and the hair. It is mainly due to the fact that these agents have a limited emulsifying power and the emulsions prepared therewith are of very reduced stability and duration. Consequently, the emulsified substances (sebum, fat and the like impurities) are deposited again on the skin and on the hair in very short times.

It is also known is this art that the thickening agents selected among the afore mentioned substances are fully unsuitable from the point of view of the hygiene and of the cleaning effect towards the skin, the scalp and the hair.

Owing to the simultaneous presence in the preparation according to the invention of such an emulsifying agent, and of such a thickening agent, the emulsifying power is relevantly increased with respect to that of the emulsifying agent or agents, if used per se, and the stability and duration of the thus obtained emulsions are increased. These emulsions can thereafter be removed as such by mean, of a simple water rinsing, whereby the cleaning action of the preparation of the invention takes place in a mild and delicate manner.

The main feature is that a modeste amount of sebum and/or of fatty substances is retained on the skin and on the scalp, which is physiologically requested for the protection, thus preventing irritating on reactive conditions from possibly occurring. As a matter of fact, both agents (emulsifying and thickening) which are simultaneously present in the preparation according to the invention, give place to a synergic action, with respect to each other and with respect to the solubilization of fatty substances, sebum and other possible impurities, as well as with respect to their removal from the skin, the scalp and the hair.

It is to be noticed that all the above mentioned compounds, which can be used either alone or in combination as the emulsifying or thickening agents in the preparation according to the invention, are readily commercially available and were known as being very well tolerated, whereby, as it is well known, they are commonly used in the preparation of skin creams, also for extended use.

A preparation according to the invention is advantageously prepared as a formulation of almost solid consistency, for example creams or gels, or with a liquid consistency such as lotions and milks. Of course, in the formulations of the preparations according to the invention, conventional auxiliary ingredients can be used for gel formulations. For the lotions, ethyl alcohol, isopropyl alcohol, propylenglycol and water are normally used.

Of course, in the formulations of preparations according to the invention also preserving agents and perfumes can be used, when desired.

For the manufacturing of the preparations of the present invention, the techniques and methods, as conventionally known in the related art, can be used.

The preparations, of the present invention are used essentially in the same manner as the normal shampooings, soaps, foam baths and other like cleaning compositions.

Some examples of formulations of the preparations according to the present invention are hereinafter reported, only ofr illustrative purpose and without limiting meaning.

| Example 1 | Cream |
|---|---|
| Sodium alginate | 2% |
| polyoxyethylenlaurylether | 7% |
| cetyl alcohol | 1.5% |
| preserving agent | as needed |
| water | as needed to 100 g |

The sodium alginate and the preservant are dissolved in water at 75° C. The polyoxyethlenlaurylether and the cetyl alcohol are separately admixed by heating to 75° C. The two phases are combined by stirring in a planetary mixer and the mixture is cooled under stirring.

| Example 2 | Gel |
|---|---|
| Carboxyvinyl polymer | 2% |
| polyoxyethylenoleylether 20 | 8% |
| propylene glycol | 5% |
| preserving agent | as needed |
| water | as needed to 100 g |

All the ingredients are dissolved in water at 75° C., and the mixture is stirred and cooled under stirring.

| Example 3 | Milk |
|---|---|
| Carboxymethylcellulose | 1% |
| polyoxyethylenated ricinoleic glyceride 40 | 9% |
| polyoxyethylen cholesterol 24 | 1.5% |
| preserving agents | as needed |
| water | as needed to 100 g |

Carboxymethylcellulose and the preservant are dissolved in water at 75° C. The polyoxyethylenated ricinoleic glyceride, and the polyoxyethylene cholesterol are separately admixed and heated to 75° C. The two phases are combined under stirring and the mixture is cooled under stirring.

| Example 4 | Lotion |
|---|---|
| Arabic gum | 1.5% |
| Polyoxyethylensorbitanmonolaurate | 7% |
| polyethylenglycol 400 | 5% |
| ethyl alcohol | 10% |
| perfume | as needed |
| water | the amount needed to 100 g. |

Arabic gum, polyoxyethylensorbitan monolaurate and polyethylene glycol are dissolved in water at 75° C. under stirring. The mixture is cooled and then the ethyl alcohol and the perfume are added.

The good local tolerability and particularly the absence of irritating action of the preparations according to the invention have been confirmed from the results of the following experiments.

A preparation according o the present invention and having the formulation of example 1 has been tested in rabbits in comparison with a preparation according to the prior art having the following composition:

| Comparison example | |
|---|---|
| Sodium laurylethersulphate | 5 g |
| alkylamides of fatty acids | 5 g |
| ethoxylated lanoline | as needed |
| water | the amount needed to 100 g. |

For the experiments two albine rabbits were used, having a body weight of about 3 kg, which were fed in a conventional manner.

The rabbits were treated with the test preparations, diluted to a 10% concentration with water, by daily frictioning (for 5 days per week) the right and left rear parts. The checking, operations as carried out weekly for two weeks, were directed to the assessing of the skin irritation state and the hair control. The following results were observed:

(A) Rabbit treated with the preparation of the prior art.

At the first checking time a strong irritation of the skin as well as a relevant hair loss was assessed, the hair being detached by tufts. At the second weekly control, the persistency of the irritation was assessed, it being however reduced in comparison with that of the preceeding control. The hair loss wass essentially total (the skin was devoid of hair).

(B) Rabbit treated with the preparation of example 1 of the invention.

No irritation of the skin and no hair loss were observed for both the weekly controls.

I claim:

1. In aqueous preparations for hygenic uses and, cleaning of skin, scalp and hair, selected from the group consisting of:
   (a) about 5 to about 10% of an emulsifying agent, and having an HLB emulsifying power of between 10 and 19; and
   (b) about 0.5 to about 5% of a thickening agent capable of forming gels and colloidal solutions in the presence of water, wherein the preparations provide a mild and delicate cleaning action, non-irritating to the skin, have a low tendency to remove fat and a reduced tendency for stimulation of sebum secretion, the improvement wherein said preparations are specifically selected from the group consisting of a milk having the composition:
      (a) 1.0% carboxymethylcellulose,
      (b) 9.0% polyoxyethylated ricinoleic glyceride 40;
      (c) 1.5% polyoxyethylene cholesterol 24, and
      (d) the remainder water;
   a cream containing:
      (a) 2.0% sodium alginate,
      (b) 7.0% polyoxethylene laurylether,
      (c) 1.5% cetyl alcohol,
      (d) the remainder water; and a lotion containing:
      (a) 1.5% arabic gum,
      (b) 7.0% polyoxyethylene sorbitan monolaurate,
      (c) 5.0% polyethyleneglycol 400,
      (d) 10.0% ethyl alcohol, and
      (e) the remainder water.

2. The aqueous preparations according to claim 1, additionally including preserving agents.

3. The aqueous preparations according to claim 1, additionally containing perfumery agents.

4. The aqueous preparations according to claim 1, made by a process wherein the carboxymethylcellulose and preserving agents are dissolved in water at about 75° C.; separately admixing and heating said polyoxyethylenated ricinoleic glyceride and the polyoxyethylene cholesterol; combining the resulting two phases to form a mixture; and agitating and cooling said mixture.

5. A method for cleaning human skin comprising the steps of:
   applying to the skin, hair or scalp a substantially aqueous preparation in cream, gel, milk or lotion form containing preserving agents and consisting essentially of:
   about 1.0% carboxymethylcellulose
   about 9.0% polyoxyethylated ricinoleic glyceride;
   about 1.5% polyoxyethylene cholesterol 24;
   and the balance being water; and removing said preparation;
   and wherein the thickening agent combines with the emulsifying agent to produce a synergistic action improving the solubilization of fatty substances, sebum other impurities present on said skin, hair and scalp.

6. In the method of claim 5, wherein said aqueous preparation is in the form of a milk and consists of:
   about 1.0% carboxymethylcellulose;
   about 9.0% polyoxyethylated ricinoleic glyceride 40;
   about 1.5% polyoxyethylene chloresterol 24; and the balance water.

7. In the method of claim 5, including the steps of making said preparation by dissolving carboxymethylcellulose and preserving agents in water at about 75° C.; separately admixing and heating a polyoxyethylenated ricinoleic glyceride 40 and the polyoxyethylene chloresterol; combining the resulting two phases to form a mixture, agitating and cooling said mixture.

* * * * *